(12) United States Patent
Wright

(10) Patent No.: US 6,698,426 B1
(45) Date of Patent: Mar. 2, 2004

(54) FACE AND TRACHEOSTOMY NEUBULIZING MASK

(76) Inventor: Vivian A. Wright, 6901 Edgewater Dr. #321, Coral Gables, FL (US) 33133

( * ) Notice: Subject to any disclaimer, the term of this patent is extended or adjusted under 35 U.S.C. 154(b) by 0 days.

(21) Appl. No.: 10/454,155

(22) Filed: Jun. 4, 2003

(51) Int. Cl.$^7$ ............................................. A61M 15/00
(52) U.S. Cl. ............................ 128/204.11; 128/200.14; 128/207.29
(58) Field of Search ................... 128/200.14, 201.11, 128/201.13, 201.27, 201.28, 203.22, 204.11, 204.12, 204.13, 204.14, 205.27, 207.29

(56) References Cited

U.S. PATENT DOCUMENTS

| 3,915,165 A | * | 10/1975 | Rambosek et al. .... | 128/203.15 |
|---|---|---|---|---|
| 4,489,723 A | * | 12/1984 | Simons et al. ......... | 128/207.16 |
| 4,938,209 A | | 7/1990 | Fry | |
| 5,647,355 A | * | 7/1997 | Starr et al. ............. | 128/205.24 |
| 5,749,360 A | | 5/1998 | Lacey et al. | |

* cited by examiner

Primary Examiner—Aaron J. Lewis
(74) Attorney, Agent, or Firm—Raymond Miller; Pepper Hamilton LLP

(57) ABSTRACT

A double-body therapeutics face and tracheostomy mask which functions as both a mask for the nose and mouth of a patient and a mask for the tracheostomy tube area of a patient is disclosed. The mask of the present invention serves as a means for delivering a gaseous medicament or a liquid, such as liquid medication, in the form of a fine spray or mist to the nose, mouth, and trachea of the patient simultaneously. The upper body of the mask fits over the nose and mouth area of the patient and the lower body of the mask fits a patient's tracheostomy tube area. The upper and lower mask bodies are connected to one another and to a nebulizing apparatus by a delivery conduit such as a standard "T" connector.

13 Claims, 2 Drawing Sheets

FACE AND TRACHEOSTOMY NEUBULIZING MASK

FIELD OF INVENTION

The present invention relates generally to apparatus in the field of respiratory therapy. More particularly, the present invention relates to a double-body therapeutics face and tracheostomy mask which functions as both a mask for the nose and mouth, as well as a mask for communication with a tracheostomy tube of a patient.

BACKGROUND

Nebulizers which produce a fine spray or mist have long been used in the treatment of various ailments and in the administration of medication. Masks have been developed which are in fluid communication with nebulizers and which are worn by the patient to more efficiently deliver the spray or mist to the nose and/or mouth of the patient. U.S. Pat. No. 4,938,209 discloses such a nebulizing mask that is equipped for the nose and/or mouth of a patient.

Additionally, patients who suffer from an obstruction in the respiratory tract are often treated with surgery to create an opening in the neck through which to breathe. The result of the surgery is a stoma or breathing hole in which the patient is often intubated with a tracheostomy tube. Such patients often require the infusion of a gaseous medicament, such as oxygen, which is supplied into the tracheostomy tube. U.S. Pat. No. 5,749,360 discloses such a tracheostomy mask.

Each of the nebulizing masks currently existing in the prior art, however, deliver the spray or mist to either the nose and/or mouth, or to the trachea. Thus, a patient needing nose, mouth, and tracheostomy nebulizing must carry out the nebulizing exercise once for the nose and mouth by way of face mask, and then repeat the process for tracheostomy nebulizing by way of a separate tracheostomy mask. Nebulizing is often necessary five to fifteen times over a twenty-separate tracheostomy mask. Nebulizing is often necessary five to fifteen times over a twenty-four hour period for twenty to thirty minutes each time to ensure that all three orifices are sufficiently nebulized. A need has therefore been felt for a double-bodied mask that allows for simultaneous nebulizing of all three orifices through a single communication incorporating the functions of two conventional masks, while allowing for increased convenience for the patient.

The present invention is directed to a double-body mask that provides the advantage of reducing patient nebulizing time by addressing both face and tracheostomy nebulizing simultaneously.

SUMMARY

Accordingly, it is an object of the present invention to provide a simultaneous nose, mouth, and tracheostomy mask.

In one embodiment, a double-body face and tracheostomy nebulizing mask providing fluid communication with a nebulizing apparatus for delivery of nebulizing medicaments, mist, spray or gaseous therapeutics simultaneously to the nose, mouth and tracheostomy tube of a patient includes an upper-body defining a rearwardly opening cavity for receiving the face of a patient and a forwardly disposed opening for receiving from a nebulizing apparatus at least one of nebulizing medicaments, spray, mist, and gaseous therapeutics, a lower body having a rear portion which terminates in an opening defined by a perimeter for receiving the neck of a patient, and a forwardly disposed opening for receiving from a nebulizing apparatus at least one of nebulizing medicaments, spray, mist, and gaseous therapeutics, where the rear portion has an interior surface that is adapted for communication with the tracheostomy tube, and a delivery conduit having at least three end portions, where the first end portion is connected to the forwardly disposed opening of the upper body, the second end portion is connected to the forwardly disposed opening of the lower body, and the third end portion communicates with the nebulizing apparatus.

A preferred embodiment of the present invention includes a moldable plastic double-body mask that is lightweight and sanitary. The mask functions as two conventional nebulizing masks, namely, a facemask and a tracheostomy mask, and serves as a means for delivering a gaseous medicament or a liquid, such as liquid medication, in the form of a fine spray or mist to the nose, mouth, and tracheostomy tube of the patient. The upper body of the mask is designed to be placed over the nose and mouth area of a patient's face, and the lower body of the mask is designed to be placed over the trachea area of the patient's neck and in communication with a tracheostomy tube.

This mask provides several advantages, including an increase in patient comfort. This is, in part, because the mask may be changed or reconfigured while the mask is still in place on the patient. This capability allows for the simultaneous nebulizing of all three orifices of the patient or the nebulizing of the nose and mouth separately from the tracheostomy nebulizing, if so desired. Another advantage of the present invention is that the mask may be manufactured from readily available materials, utilizing common manufacturing technologies and techniques.

DESCRIPTION OF THE DRAWINGS

In part, other aspects, features, benefits and advantages of the embodiments of the present invention will be apparent with regard to the following description, appended claims and accompanying drawings where:

DETAILED DESCRIPTION

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods, devices, and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

The present invention provides a double-body therapeutics face and tracheostomy mask, including an upper body and a lower body, which functions as both a mask for the nose and the mouth, as well as a mask for the trachea of the patient. The mask of the present invention serves as a means for delivering gaseous medicament or liquid, such as liquid medication, in the form of a fine spray or mist to the nose, mouth, and tracheostomy tube of the patient.

Figure 1:
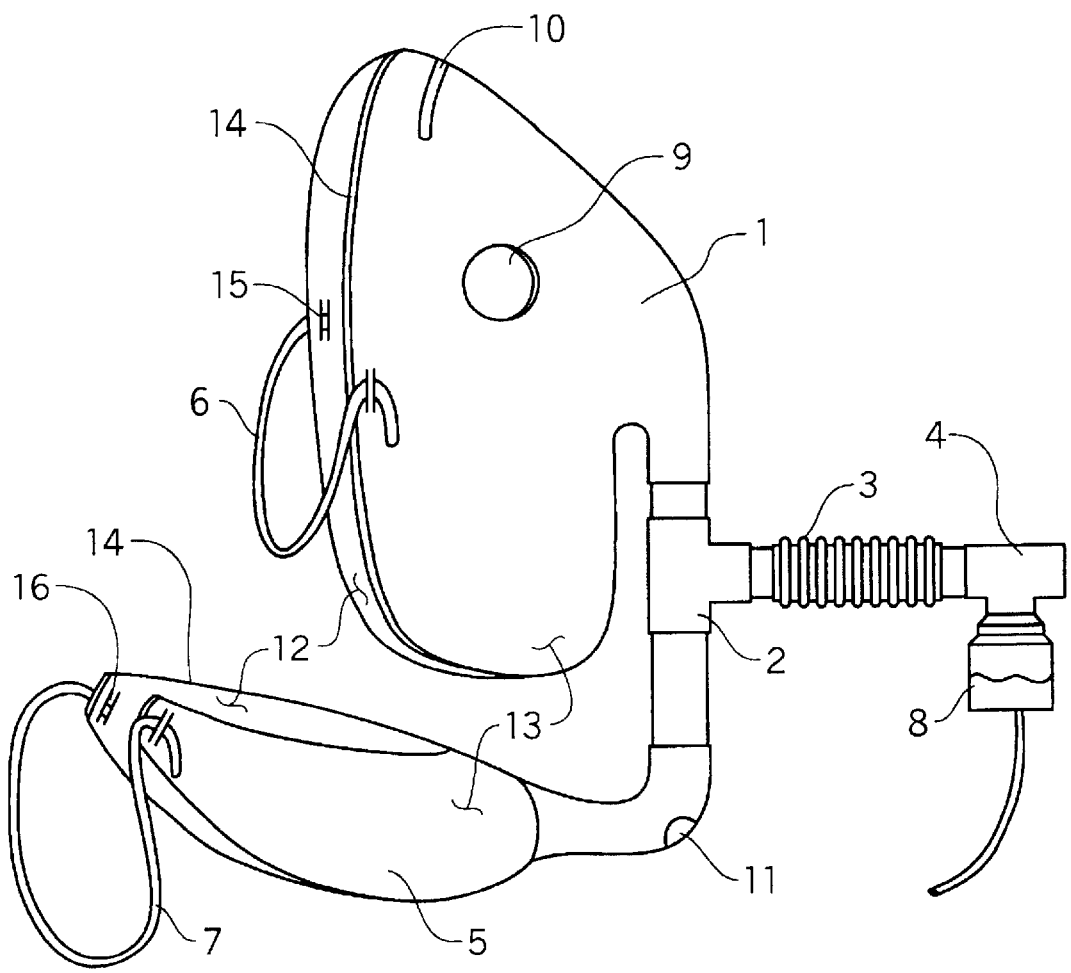
FIG. 1 illustrates a side view of a preferred embodiment of the present invention.

The double-body mask according to one embodiment of the present invention is illustrated in the side view in FIG. 1. The mask is preferably made of a soft, flexible, clear material. The upper body 1 of the mask of the present invention is flexible and has an interior surface 12 and an exterior surface 13 and is designed to be placed over the nose and mouth area of a patient's face. The upper body 1 of the mask is secured to the patient's face by way of an elastic strap 6 that goes around the back of the head. When applied to the patient, the interior surface 12 is in communication with the patient and the exterior surface 13 is in communication with the ambient atmosphere. The lower body 5 of the mask of the present invention is flexible, is designed to be placed over the trachea area of the patient's neck and to communicate with the tracheostomy tube, and is secured by way of an elastic strap 7 that goes around the neck. The upper body 1 and the lower body 5 of the mask of the present invention are each formed in the shape of a substantially continuous, cup shaped wall. The elastic straps 6, 7 may be fixed to the upper body 1 and lower body 5 of the mask by any conventional means, such as threading the straps through parallel slots 15, 16. Alternatively, snaps, VELCRO, hook and loop fasteners, clips, or any other conventional means may be used. Once the upper body 1 of the mask is secure against the face of the patient, a clip 10, preferably made of aluminum, is placed on the nose area of the mask of the patient in order to provide a closer fit around the nose and cheek area.

The upper body 1 of the mask of the present invention is connected to the lower body 5 of the mask of the present invention by a delivery conduit 2, preferably any 'T' connector which is known in the art. One end of the T connector 2 is attached to the upper body 1 of the mask. A second end of the T connector 2 is attached to the lower body 5 of the mask. The third end of the T connector 2 is attached to one end of, preferably, a pliable hollow accordion tube 3. Alternatively, the third end of the T connector 2 may be attached to hollow smooth tubing or any other conventional hollow tube. The other end of the hollow accordion tube 3 is connected to a nebulizing apparatus 4, such as a nebulizing cup, which is designed to atomize a liquid 8, such as a liquid medication, to produce a fine spray or mist. Thus, a delivery conduit 2 defines a passageway there through for fluid communication between the nebulizing apparatus 4 and the patient for spray and mist to reach the face and the tracheostomy tube. The nebulizing apparatus 4 is connected to a nebulizing machine from which airflow meets the nebulizing medicaments 8 to produce mist or spray. The end of the T connector 2 that is attached to the lower body 5 of the mask also contains an opening 11, or vent, in order to help alleviate a build-up of condensation within the hollow accordion tube 3 and T connector 2.

The upper body 1 of the mask of the present invention defines a rearwardly opening cavity for receiving the face of the patient, and a forwardly disposed opening for receiving the T connector 2. The T connector 2 is positioned so that, when the mask is worn by the patient, it is located below the nose of the patient. The upper body 1 also includes two vent holes 9 in order to help prevent condensation from building up inside the mask.

The lower body 5 of the mask of the present invention is flexible and has an interior surface 12 and an exterior surface 13. The lower body 5 of the mask is formed in a continuous, cup shaped wall and includes a rear portion which terminates in an opening defined by a perimeter 14. The perimeter 14 is sized and shaped for sealable engagement against the neck, tracheostomy tube, and stoma hole of the patient. The cup-shaped wall 14 of the lower body of the mask extends away from the rear portion and terminates in a forward portion which is connected to the T connector 2. Preferably, the lower body 5 tapers throughout this extension. The interior surface 12 is in communication with a tracheostomy tube when the mask is engaged on the neck of the patient. The lower body 5 also includes a vent hole 11 in order to help prevent condensation from building up inside the mask.

Figure 2:
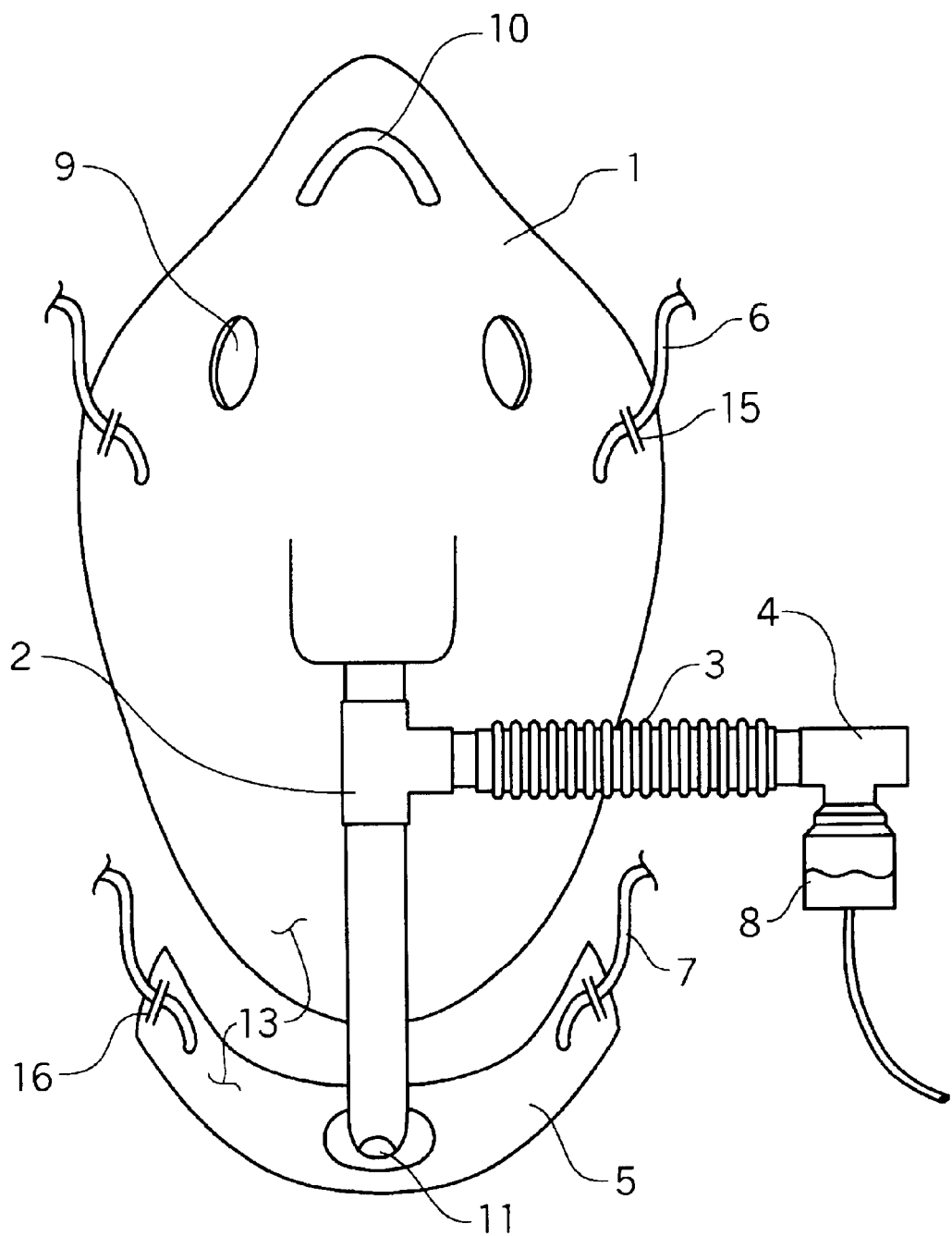
FIG. 2 illustrates a frontal view of a preferred embodiment of the present invention.

In FIG. 2, the double-body mask of the present invention is illustrated according to a frontal view. This view illustrates that the double-body mask includes two flexible mask bodies 1, 5. Again, the upper body 1 of the mask of the present invention is connected to the lower body 5 of the mask of the present invention by any 'T' connector 2 which is known in the art. One end of the T connector 2 is attached to the upper body 1 of the mask. A second end of the T connector 2 is attached to the lower body 5 of the mask. The third end of the T connector 2 is attached to one end of, preferably, a pliable hollow accordion tube 3. The other end of the hollow tube 3 is connected to a nebulizing apparatus 4, such as a nebulizing cup, which is designed to atomize a liquid 8, such as a liquid medication, to produce a fine spray or mist. Thus, a delivery conduit 2 defines a passageway there through for fluid communication between the nebulizing apparatus 4 for spray and mist to reach the face and the tracheostomy tube. The nebulizing apparatus 4 is connected to a nebulizing machine from which airflow meets the nebulizing medicaments 8 to produce mist or spray. The end of the T connector 2 that is attached to the lower body 5 of the mask also contains an opening 11, or vent, in order to help alleviate a build-up of condensation within the hollow tube 3 and T connector 2.

What is claimed is:

1. A double-body face and tracheostomy nebulizing mask providing fluid communication with a nebulizing apparatus for delivery of nebulizing medicaments, mist, spray or gaseous therapeutics to the nose, mouth, and tracheostomy tube of a patient, said mask comprising:

an upper body defining a rearwardly opening cavity for receiving the face of a patient and a forwardly disposed opening for receiving from a nebulizing apparatus at least one of nebulizing medicaments, spray, mist, and gaseous therapeutics;

a lower body having a rear portion which terminates in an opening defined by a perimeter for receiving the neck of a patient, and a forwardly disposed opening from a nebulizing apparatus at least one of nebulizing medicaments, spray, mist, and gaseous therapeutics, wherein the rear portion has an interior surface that is adapted for communication with the tracheostomy tube;

a delivery conduit having at least three end portions, wherein the first end portion is connected to the forwardly disposed opening of the upper body, the second end portion is connected to the forwardly disposed opening of the lower body, and the third end portion communicates with the nebulizing apparatus.

2. The double-body face and tracheostomy nebulizing mask of claim 1 wherein the third end of the delivery conduit is attached to one end of a hollow tube, and a second end of the hollow tube is connected to the nebulizing apparatus.

3. The double-body face and tracheostomy nebulizing mask of claim 1 wherein the nebulizing apparatus is a nebulizing cup.

4. The double-body face and tracheostomy nebulizing mask of claim 1 wherein the delivery conduit contains an opening to drain condensation.

5. The double-body face and tracheostomy nebulizing mask of claim 1 wherein the upper body contains a plurality of openings to drain condensation.

6. The double-body face and tracheostomy nebulizing mask of claim 1 wherein the perimeter of the lower body is sized and shaped for sealable engagement against the neck of a patient.

7. The double-body face and tracheostomy nebulizing mask of claim 1 wherein the lower body contains at least one opening to drain condensation.

8. The double-body face and tracheostomy nebulizing mask of claim 1 wherein the upper body contains an upper-body strap that fits around the head of the patient, and the lower body contains a lower-body strap that fits around the neck of the patient.

9. The double body face and tracheostomy nebulizing mask of claim 8 wherein the upper-body strap is elastic.

10. The double-body face and tracheostomy nebulizing mask of claim 1, wherein the mask is operable to selectively deliver the nebulizing medications, mist spray or gaseous therapeutic to any one or more of the nose, mouth, and tracheostomy tube of the patient.

11. The double-body face and tracheostomy nebulizing mask of claim 1 wherein the upper body includes a means for securing the face mask snuggly to the face of the patient.

12. The double-body face and tracheostomy nebulizing mask of claim 11 wherein the means for securing the face mask snuggly to the face of the patient is a nose clip.

13. The double-body face and tracheostomy nebulizing mask of claim 12 wherein the nose clip comprises aluminum.

* * * * *